(12) United States Patent
Coufal

(10) Patent No.: US 6,603,001 B1
(45) Date of Patent: Aug. 5, 2003

(54) PROCESS FOR PREPARING SOLID MELAMINE

(75) Inventor: Gerhard Coufal, Leonding (AT)

(73) Assignee: Agrolinz Melamin GmbH, Linz (AT)

(*) Notice: Subject to any disclaimer, the term of this patent is extended or adjusted under 35 U.S.C. 154(b) by 0 days.

(21) Appl. No.: 09/913,465

(22) PCT Filed: Mar. 8, 2000

(86) PCT No.: PCT/EP00/02012

§ 371 (c)(1), (2), (4) Date: Aug. 30, 2001

(87) PCT Pub. No.: WO00/55142

PCT Pub. Date: Sep. 21, 2000

(30) Foreign Application Priority Data

Mar. 15, 1999 (AT) ............................................. 451/1999
Mar. 15, 1999 (AT) ............................................. 450/1999

(51) Int. Cl.$^7$ .............................................. C07D 251/62
(52) U.S. Cl. ....................................... 544/201; 544/203
(58) Field of Search ................................. 544/201, 203

(56) References Cited

FOREIGN PATENT DOCUMENTS

| AT | A 159/98 | 1/1998 |
|---|---|---|
| AU | 709030 | 6/1997 |
| EP | 0 808 836 | 11/1997 |
| WO | 97/20826 | 6/1997 |
| WO | 97/47609 | 12/1997 |

*Primary Examiner*—John M. Ford
*Assistant Examiner*—Venkataraman Balasubramanian
(74) *Attorney, Agent, or Firm*—Wenderoth, Lind & Ponack, L.L.P.

(57) ABSTRACT

The invention relates to a method for producing solid melamine by expanding liquid, ammoniacal melamine which is mixed with excess ammonia, whereby a dispersion is produced. Said dispersion is expanded, optionally after it has been held under ammonia pressure, whereby solid melamine is deposited. The solid melamine is optionally held under ammonia pressure. Expansion is then optionally carried out in any particular order, along with cooling to room temperature and the pure melamine is isolated.

19 Claims, No Drawings

PROCESS FOR PREPARING SOLID MELAMINE

The invention relates to a process for preparing solid melamine, by depressurizing a dispersion of ammonia and liquid melamine, whereupon solid melamine precipitates.

Melamine is preferably prepared by pyrolyzing urea, using either low-pressure processes or high-pressure processes, for example those described in "Ullmann's Encyclopedia of Industrial Chemistry, Vol A 16, 5th ed (1990), pp. 171–185". Depending on the preparation process, the melamine synthesized comprises from about 94 to 98% by weight of melamine, and also in particular melam, melem, ureidomelamine, ammeline, and ammelide as significant impurities, and has to be further purified through particular steps of the process for the more demanding application sectors. To obtain solid melamine, the liquid melamine melt may be cooled, for example using water, using aqueous melamine-containing solutions or suspensions, or using cold inert solids or solid melamine, as in AT 159/98, for example in a fluidized bed. A particularly advantageous method is to inject and depressurize an ammonia-containing melamine melt, for example as in WO97/20826, into a cooling vessel, in which an atmosphere of ammonia is present, whereupon pure solid melamine precipitates. However, this process does not give ideal results under all conditions of pressure and temperature.

The object was therefore to find a process which, irrespective of the temperature used and of the pressure used, gives solid melamine of good quality via depressurization, and in a wide range of temperature and of pressure, and in particular at low melt pressures.

It has now been found that this object can be achieved in that the melamine melt to be depressurized comprises excess ammonia in addition to the dissolved ammonia, giving a two-phase mixture in the form of a dispersion of ammonia and liquid melamine.

The invention therefore provides a process for preparing solid melamine by depressurizing liquid, ammonia-containing melamine, characterized in that a) the liquid ammonia-containing melamine is mixed with excess ammonia, whereupon a dispersion of ammonia and liquid melamine forms, b) where appropriate, the dispersion is aged under the pressure generated by ammonia, c) the dispersion is depressurized, whereupon solid melamine precipitates, d) where appropriate, the solid melamine is aged under the pressure generated by ammonia, e) and then, where appropriate and in any desired sequence, there is further depressurization to atmospheric pressure, and cooling to room temperature, and the melamine is isolated.

The ammonia (gas phase) is preferably supercritical and is preferably in finely dispersed form in the liquid melamine melt (liquid phase) producing a very finely dispersed "melamine foam". The mixing process forms a dispersion of melamine and ammonia, the liquid melamine becoming saturated with ammonia. It is preferable for the liquid melamine phase to have been saturated with ammonia. According to the invention it is possible either for the ammonia to have been dispersed in the liquid melamine or for the liquid melamine to have been dispersed in the ammonia. It is important that the entire amount of ammonia (dissolved ammonia and ammonia present in the gas phase) is sufficiently great for the amount of heat dissipated during the depressurization to be that needed to solidify the melamine. A particular advantage of the invention is therefore that with the aid of the excess ammonia dispersed in the melt it is possible to obtain sufficient dissipation of heat to solidify the melamine during the depressurization even at relatively low pressures on, and relatively high temperatures of, melamine melts where relatively little ammonia has been dissolved in the melamine melt. The amount of excess ammonia in the melamine melt depends in particular on the level of temperature of, pressure on, and ammonia saturation of the melt prior to the depressurization, and on the extent to which the melamine is to be cooled below its melting point once it has been solidified. High temperatures of, and low pressures on, the melt therefore require larger amounts of excess ammonia than temperatures which are just above the melting point of the melamine, which depends on the ammonia pressure used. On the other hand, high pressures necessitate smaller amounts of excess ammonia. The amount of excess ammonia may therefore vary within wide limits.

Since the melting point of the melamine at lower pressures after depressurization is higher than at high pressures, it is also possible according to the invention—in particular if the temperature of the melt is not too far above the melting point, which depends on the pressure, and the amount of excess ammonia is not very great—that the temperature during solidification remains the same or even rises.

According to the invention, it is preferable that the pressures at which the liquid ammonia-containing melamine is mixed with ammonia are from about 50 to 1000 bar, and that the liquid ammonia-containing melamine is then depressurized to a pressure of from about 1 to 200 bar, whereupon solid melamine precipitates. Depending on the procedure selected, the pressure both prior to and after the depressurization may vary over a wide range. The upper pressure limit prior to the depressurization is preferably about 600 bar, preferably about 350 bar or about 250 bar. However, the upper limit may also be about 150 bar or about 130 bar. The lower pressure limit prior to the depressurization is preferably from about 60 to 80 bar. The pressure after the depressurization may likewise vary within a wide range. If an annealing process follows immediately, depressurization takes place to relatively high pressures, otherwise depressurization to atmospheric pressure is possible. The pressure after the depressurization is therefore preferably from about 1 to 100 or 150 bar, particularly preferably from about 1 to 60 bar. However, it may also be from about 10 to 20 bar.

During the mixing with ammonia, or prior to the depressurization, the temperature of the liquid ammonia-containing melamine is preferably in the range from about 60° C. above the melting point of the melamine, which depends on the ammonia pressure used, to just above the melting point of the melamine, which depends on the ammonia pressure used, particularly preferably at temperatures between about 1 and 40° C., very particularly preferably between 1 and 20° C., above the melting point of the melamine, which depends on the ammonia pressure used. The most useful temperature is only very slightly above the melting point of the melamine, which depends on the ammonia pressure used. The desired depressurization temperature is most particularly preferably below about 350° C. It is preferable for the liquid, ammonia-containing melamine to have been saturated with ammonia.

Suitable mixing equipment can be used for mixing the liquid, ammonia-containing melamine with excess ammonia, forming a dispersion, for example mixers, stirrers, reactors with naturally aspirated stirrers, or static mixers, injectors, ejectors, or other suitable mixing equipment. The melamine melt may be mixed with either gaseous or liquid ammonia, but if liquid ammonia is used the melt must not solidify. The temperature of the melt preferably lowers during this process and is thus brought into the vicinity of the desired temperature, or to the desired temperature.

Prior to the depressurization, either the pressure or the temperature may, where appropriate, be increased, lowered or held constant, using any desired method, either prior to or else after the mixing of melamine with ammonia, but the melt must not solidify during this process. To achieve a particularly good quality of melamine, it is advantageous for the liquid melamine melt to be aged under the pressure generated by ammonia prior to the depressurization, either prior to or after the mixing of the liquid melamine and ammonia. This preferably takes place for from about 1 min to 10 h depending on the process conditions selected in the temperature range from about 350° C. to just above the melting point of the melamine, which depends on the ammonia pressure used, and preferably at temperatures above the melting point of the melamine, which depends on the ammonia pressure used, by from about 1 to 60° C., particularly preferably by from about 1 to 40° C., more particularly preferably by from about 1 to 20° C. It is advantageous here to lower the temperature of the liquid melamine, for example by introducing liquid or gaseous ammonia. The pressure during the aging process here is in the range from about 50 to 1000 bar, preferably from about 80 to 600 bar, particularly preferably from about 130 to 400 bar. If the aging takes place after the mixing of melamine and ammonia, care must be taken that the dispersion is retained during the aging process.

The temperature at which the dispersion of ammonia and liquid melamine is depressurized is preferably above the melting point of the melamine, which depends on the ammonia pressure used, by from about 1 to 60° C., particularly preferably from about 1 to 40° C., more particularly preferably by from about 1 to 20° C., whereupon the solid melamine deposits, its melting point now being higher at lower pressure.

In a first embodiment of the invention, the depressurization of the melamine-ammonia dispersion follows the mixing process. Additional ammonia may also be introduced at this stage. It is preferable for the dispersion to be depressurized into a separate, and where appropriate heated, container, in which an atmosphere of ammonia is present. The melamine dispersion here may be sprayed into the container via nozzles, e.g. single-fluid nozzles, twin-fluid nozzles or venturi nozzles, or via injectors or ejectors, for example.

In another embodiment of the invention, it is also possible for the liquid melamine or a dispersion of melamine and ammonia to be mixed with the excess ammonia during depressurization. This preferably takes place in specific mixing and conveying apparatuses, for example in injectors or ejectors, in which the ammonia, as propellant gas, mixes with the liquid melamine, or liquid melamine, as propellant medium, mixes with ammonia, and the resultant dispersion is simultaneously conveyed, with pressure drop, into the depressurization container.

Following the depressurization, it is also possible for the solid melamine to be agitated, for example by stirring or by depressurizing the melamine melt into a rotating drum or into a fluidized bed, for example, with solidification.

The temperature of the melamine may either become lower or become higher, or else remain the same through the depressurization. Especially when using a relatively large excess of ammonia, the temperature of the solid melamine after depressurization is mostly lower than the temperature of the dispersion prior to the depressurization. However, according to the invention and due to the relatively high melting point of melamine at relatively low pressures, it is also possible and particularly advantageous for the temperature of the solid melamine after the depressurization to remain the same or even to rise, due to the heat of crystallization liberated.

It has also proven advantageous for the melamine also to be aged after the solidification process, under the pressure generated by ammonia. During this process, after the depressurization, the solid melamine is aged in an atmosphere of ammonia, where appropriate with mechanical stirring or in a rotating drum or through pneumatic agitation, for example in a fluidized bed, for example for from about 10 sec to 20 h, preferably for from about 1 min to 2 h, in the temperature range from about 150° C. to the melting point of the melamine, which depends on the ammonia pressure used. The residence time in the annealing process may become shorter as the temperature and pressure become higher. This temperature is preferably very slightly below the melting point, which depends on the ammonia pressure used, advantageously by up to 10° C., particularly preferably by up to 5° C. The pressure after the depressurization may vary over a wide range. If annealing follows directly, depressurization takes place to a relatively high pressure, but otherwise depressurization to atmospheric pressure is possible. The pressure after the depressurization is therefore preferably from about 1 to 150 or 100 bar, particularly preferably from about 1 to 60 bar. However, it may also be from about 10 to 20 bar. If the temperature during the depressurization and solidification remains the same or rises, it is advantageous for the solid melamine forming during this process from the melamine melt to be aged (annealed) under the conditions of temperature and of pressure at which it precipitates after the depressurization.

The process of the invention can give melamine of purity above 99% by weight. Depending on the conditions of temperature and of pressure selected prior to and during the depressurization, it is also possible to obtain melamine with a purity of up to 99.9% by weight, in some cases above 99.99% by weight, and it is particularly advantageous here to use high ammonia pressures, and also temperatures near to the melting point of the melamine.

The process of the invention may be carried out either batchwise or continuously. The process is preferably suitable to follow a process for preparing melamine, in particular to follow any desired high-pressure process for preparing melamine from urea in which the melamine is first produced in liquid form, as a melt. High-pressure processes usually give melamine in liquid form, as a melt, at pressures of from about 70 to 800 bar and at temperatures—depending on the pressure selected—of at least about 360° C. The exhaust gases arising during melamine synthesis, in particular $NH_3$, $CO_2$, and gaseous melamine, are usually scrubbed by being passed through a urea melt. During this process, the urea melt is heated by the hot exhaust gases and is advantageously passed into a melamine reactor for melamine synthesis, while the purified exhaust gases are advantageously passed into a urea reactor. The exhaust gases may either be directly passed into the urea reactor or are condensed, for example with the aid of ammonium carbonate solutions or ammonium carbamate solutions, for example those produced in the melamine plant or in the urea plant. One way of using the heat arising is for preheating the ammonia used in the urea plant, or for producing steam.

Once the exhaust gases have been removed, the melamine melt may advantageously be stripped, for example using $NH_3$, this process primarily removing residual $CO_2$. It is moreover advantageous to age the melamine melt in an aging container. However, it is also possible for the melamine melt emerging from the reactor to be mixed directly with excess ammonia once the exhaust gases have been removed.

The advantage of the process of the invention is primarily that, whatever the degree of saturation of the melamine melt with dissolved ammonia, this depending on the pressure used and on the temperature used, it is possible, in addition, to introduce a variable amount of ammonia into the melamine melt. This permits simple control, over a wide range, of the temperature used during the depressurization of the melamine melt, as required by process-related and product-related requirements, and depending on the amount of excess ammonia in the melt. The process also permits, for example, solid melamine of good quality to be produced, even at low pressures. A further advantage is the versatility to produce melamine in the purity required for the relevant applications. If no cooling takes place during the solidification process, there is the additional advantage that any annealing carried out requires no, or only little, introduction of additional heat.

What is claimed is:

1. A process for preparing solid melamine by depressurizing liquid ammonia-containing melamine, wherein:
   a) the liquid ammonia-containing melamine is mixed with excess ammonia, whereupon a dispersion of gaseous ammonia and liquid melamine forms,
   b) optionally, the dispersion is aged under the pressure generated by ammonia,
   c) the dispersion is depressurized, whereupon solid melamine precipitates,
   d) optionally, the solid melamine is aged under the pressure generated by ammonia,
   e) and then, optionally and in any desired sequence, there is further depressurization to atmospheric pressure, and cooling to room temperature, and the melamine is isolated.

2. The process as claimed in claim 1, wherein the liquid ammonia-containing melamine is mixed with excess ammonia and simultaneously depressurized, whereupon solid melamine precipitates.

3. The process as claimed in claim 2, wherein the mixing of the liquid ammonia-containing melamine with excess ammonia takes place with simultaneous depressurization with the aid of injectors or of ejectors.

4. The process as claimed in claim 1, wherein solid melamine precipitates during depressurization at the same temperature, or with an increase in the temperature.

5. The process as claimed in claim 1, wherein the liquid ammonia-containing melamine has been saturated with ammonia.

6. The process as claimed in claim 1, wherein the pressure at which the liquid ammonia-containing melamine is mixed with excess ammonia is from about 60 to 600 bar and the liquid ammonia-containing melamine is then depressurized to a pressure of from about 1 to 60 bar, whereupon solid melamine precipitates.

7. The process as claimed in claim 6, wherein the pressure at which the liquid ammonia-containing melamine is mixed with excess ammonia is from about 80 to 350 bar, and the liquid ammonia-containing melamine is then depressurized to a pressure of from about 1 to 20 bar, whereupon solid melamine precipitates.

8. The process as claimed in claim 1 wherein the temperature range within which the liquid ammonia-containing melamine is mixed with excess ammonia from about 60° C. above the melting point of the melamine, which depends on the ammonia pressure used, to just above the melting point of the melamine, which depends on the ammonia pressure used.

9. The process as claimed in claim 8, wherein the temperature range within which the liquid ammonia containing melamine is mixed with excess ammonia is from about 1 to about 20° C. above the melting point of the melamine, which depends on the ammonia pressure used.

10. The process as claimed in claim 1, wherein it is downstream of a continuous high-pressure process for preparing melamine from urea.

11. The process as claimed in claim 1, wherein the depressurization takes place in a separate container in which an atmosphere of ammonia is present.

12. The process as claimed in claim 1, wherein additional ammonia is introduced during the depressurization.

13. The process as claimed in claim 1, wherein the liquid ammonia-containing melamine is aged under the pressure generated by ammonia prior to the depressurization.

14. The process as claimed in claim 13, wherein the liquid ammonia-containing melamine is aged under the pressure generated by ammonia prior to the depressurization for about 1 minute to 10 hours at a pressure which is from about to 1 to 20° C. above the melting point of the melamine, which depends on the ammonia pressure used.

15. The process as claimed in claim 1, wherein the dispersion of ammonia and liquid melamine is depressurized at a temperature which is from about 1 to 20° C. above the melting point of the melamine, which depends on the ammonia pressure used.

16. The process as claimed in claim 1, wherein after the depressurization, the solid melamine is aged in an atmosphere of ammonia for from about 1 minute to 2 hours, in a temperature range from about 150° C. to the melting point of the melamine, which depends on the ammonia pressure used.

17. The process as claimed in claim 1, wherein the mixing of the liquid ammonia-containing melamine with excess ammonia, forming a dispersion, takes place with the aid of stirrers, static mixers, injectors or ejectors.

18. The process claimed in claim 1, wherein in step a) a dispersion of gaseous ammonia in liquid melamine is formed.

19. The process as claimed in claim 1, wherein in step a) a dispersion of liquid melamine in gaseous ammonia is formed.

* * * * *